United States Patent [19]

Richards et al.

[11] Patent Number: 4,846,004
[45] Date of Patent: Jul. 11, 1989

[54] STREAMLINED OCEANOGRAPHIC SAMPLING BOTTLE

[75] Inventors: Dennis L. Richards; Humfrey Melling, both of Victoria, Canada

[73] Assignee: Canadian Patents & Development Limited, Ottawa, Canada

[21] Appl. No.: 222,566

[22] Filed: Jul. 21, 1988

[30] Foreign Application Priority Data

Sep. 25, 1987 [CA] Canada .................................. 547,933

[51] Int. Cl.⁴ .............................................. G01N 1/12
[52] U.S. Cl. .............................. 73/864.63; 73/864.67
[58] Field of Search ............ 73/864.61, 864.63–864.67

[56] References Cited

U.S. PATENT DOCUMENTS 2,298,627 10/1942 Proudman et al. ............... 73/864.63
3,276,266 10/1966 Auer .................................. 73/864.63
4,271,704 6/1981 Peters .............................. 73/864.63

FOREIGN PATENT DOCUMENTS 0626383 9/1978 U.S.S.R. ........................... 73/864.67
0981857 12/1982 U.S.S.R. ........................... 73/864.67

Primary Examiner—Stewart J. Levy
Assistant Examiner—Robert R. Raevis
Attorney, Agent, or Firm—Ronald G. Bitner

[57] ABSTRACT

An oceanographic sampling bottle providing low drag for a rapid descent rate and low susceptibility to leakage after sample acquisition. The sampling bottle comprises streamlined inlet and outlet valve members shaped and positioned to avoid flow separation. The bottle with valves occupies a relatively small cross-sectional area facilitating design of a rosette or cluster of bottles. A hollow resilient conduit interconnecting the inlet and outlet valves draws the valves against seats on the sampling bottle when released. Vents in the conduit provide pressure equalization.

6 Claims, 1 Drawing Sheet

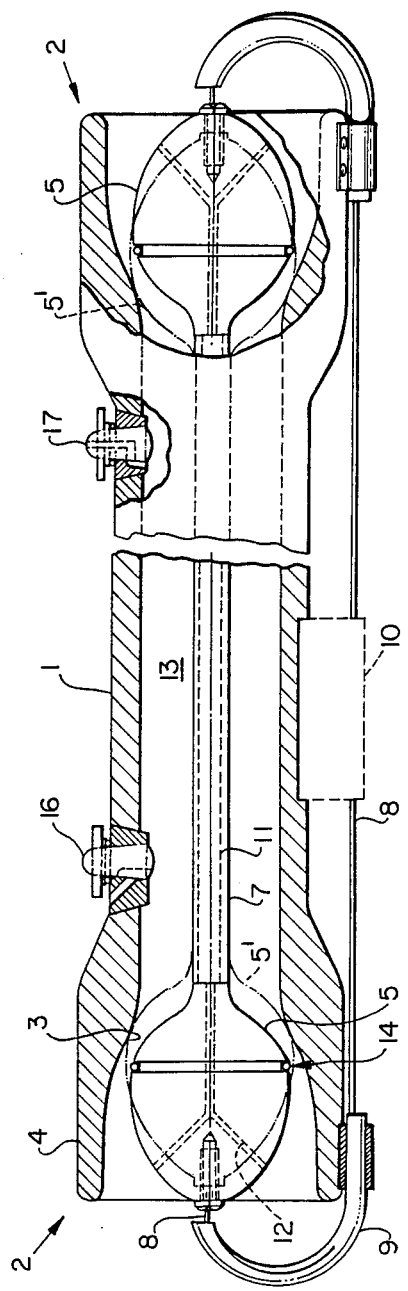
FIG. I

STREAMLINED OCEANOGRAPHIC SAMPLING BOTTLE

FIELD OF THE INVENTION

The invention relates to an oceanographic water sampling bottle.

BACKGROUND OF THE INVENTION

Current practice is seawater sampling requires sample acquisition in conjunction with the use of vertically profiling electronic sensors on a probe such as the CTD (conductivity-temperature-depth) probe. Sampling bottles are therefore clustered near the probe in a sampling rosette where their closure can be triggered electro-mechanically by the operator or a computer at the surface. Normally, rosette and probe fall through the water at about 0.5 m/s, but higher fall rates are very desirable in order to minimize the use of expensive station (aircraft or ship) time. The major limitation on descent speed and attitudinal stability of the assembly is the fluid drag associated with the sampling bottles in the rosette.

In typical prior devices considerable drag is associated with the closure mechanism for the sampling bottles. Typically, the closure mechanism of prior sampling bottles comprises hinged caps that pivot outwardly from the bottle periphery presenting a larger cross-sectional area to the flow and producing flow separation and stagnant regions within and around the bottles which both result in increased drag.

Although fluid drag can be reduced by decreasing the number of bottles on the rosette, this increases the required number of casts to complete a profile and hence increases station time.

An additional problem in current practice is leakage of seawater into a sample following its acquisition. Sample contamination through leakage is critically detrimental to salinity determination. Leakage occurs in response to pressure differences between the inside of a bottle and its environment as a result of changing ambient pressure during the profiling procedure.

During water sampling in winter in frozen polar seas, ice accumulation in the bottle interior, either when the bottle is initially immersed following chilling in the atmosphere or when the bottle and the contained sample are retrieved, causes sample contamination or irreversible changes in the salinity and chemical composition of the sample.

For water sampling in Arctic seas a sampling device with a cross-section of less than about 10 inches is advantageous as holes of such size can be augered with manually operated equipment. With presently available bottles only one bottle can be used per cast through such auger holes.

SUMMARY OF THE INVENTION

The present invention provides a water sampling bottle comprising; a tubular container defining member having an inlet and outlet end; each end having an inner surface portion defining an annular valve seat; closure means, comprising a pair of streamlined valve members one of which is associated with each of the said inlet and outlet end and disposed for operatively seating against the respective valve seat; releasable retaining means for releasably retaining the valve members away from its respective valve seat whereby the tubular member defines an open conduit prior to sample acquisition; a resilient connecting member biasing said valve members toward one another onto its respective seat, and operative to confine a sample within the tubular member upon release of said retaining means.

BRIEF DESCRIPTION OF THE DRAWING

FIG. 1 is a partly sectioned view of the water sampling bottle of the present invention.

DESCRIPTION OF THE PREFERRED EMBODIMENT

With reference to FIG. 1, the oceanographic sampling bottle comprises a tubular member 1 in which each of the open ends 2 define an inlet or outlet. An inner surface portion 3 of each end 2 defines an annular valve seat for a valve member 5 that provides closure means for the sampling bottle. The valve members are shown in the open position 15, and the closed position 15. The valve members 5 have a streamlined shape and are positioned coaxially with respect to the tubular member 1. Preferably the valve members and the tubular member will have a circular cross-sectional shape.

Preferably, the tubular member 1 is provided with an enlarged streamlined end portion 4 which surrounds and protects the valve member 5 and facilitates streamlined flow around the valve member. In order to provide streamlined flow, the size and shape of the enlarged portion 4 and valve member 5 should be chosen such that the cross-sectional area of the flow passage around the valve member 5, perpendicular to the flow, should be substantially constant and substantially equal to the cross-sectional flow area 913) through the tubular member 1.

The valve members 5 are interconnected by resilient connecting means 7 that bias the members 5 toward one another onto the respective seats 3.

For each of the valve members 5, there is provided releasable retaining means shown in the form of a cable 8 for releasably retaining the valve away from the seat. The cable 8 is guided by suitable guide means 9 attached to the member 1 and is controlled remotely by a suitable trip mechanism 10 of a conventional type.

The resilient connecting means 7 is shown in the form of a resilient tubular conduit having a passageway 11 that vents by interconnecting passageway 12 to a region outside of the seat, and outside of the sample confining region 13.

The valve members 5 have a hydrodynamically streamlined shape to avoid flow separation and resistance within and around the sampling bottle when the members are in the unseated open position for the descent. The closure members may be provided with additional sealing means, shown in the form of an O-ring 14 to ensure sealing the contents when in the seated closed position 15.

The sampling bottle is shown with a drain valve 16 and vent 17 (both shown in the open position) to facilitate recovery of the sample. These valves will preferably have low displacement to minimize the trapped volume and hence minimize possible contamination of the sample.

In operation, with reference to FIG. 1, the procedure for use may be similar to current practice. Typically a plurality of sampling bottles are grouped in the form of a rosette. The valve members 5 are open, and the drain and vent valves 16 and 17 are closed, during the descent to the desired sampling depth.

With the present invention, it can be seen that the open bottles present an hydrodynamically streamlined geometry which provides a relatively high descent rate. The reduction in drag is achieved by two means: Firstly, the valve members of the sampling bottles remain axially centered on the tubular body 1 when the bottle is open rather than being hinged out to occupy adjacent space as in other prior design; secondly, the two valves are designed to allow them being disposed within the sampling bottle wall, whereas in other prior designs, valves are bulky and project beyond the periphery. Efficient flow of seawater through the sampling bottle during descent, is achieved by the streamlined shape and relative positioning of the valve members and of the inlet/outlet ends to ensure non-separated flow through the annular regions surrounding the valve members, and minimizing stagnant regions.

When the desired depth is reached, one or more of the sampling bottles are closed by release of the retaining means 10 in a conventional manner. Upon release both of the pair of closure members 5 are forced onto the respective seat 3 by the force of the resilient interconnecting means 7 to the position 5'.

Equalization of the pressure of the sample and of the ambient fluid is achieved by venting the hollow centre 11 of the resilient tubular conduit 7 (which also provides the tension holding the closure members in place) outside through passageways 12. Since the tubing is resilient, over- or under-pressure within the sampling bottle, which might otherwise occur during profiling, is avoided and sample seating is more readily obtained.

The present sampling bottle, by having the valve members confined to the bottle, occupies a relatively small cross-sectional area, as compared with previous designs, and thus also allows a more compact rosette or cluster of bottles.

The present streamlined design, specifically the reduction of projecting parts, makes the present sampling bottle less susceptible to ice accretion in polar applications.

To maximize the thermal inertia of the sampling bottle, it will preferably be constructed of a material (e.g. plastic) having low thermal diffusivity, and a wall thickness as large as possible consistent with other design requirements.

A material found to have suitable properties for the sampling bottle is polymethylpentene. This material has suitable thermal properties and low absorption and hence minimal susceptibility to contamination.

What is claimed is:

1. An oceanographic sampling bottle comprising:
    a tubular container defining member having a streamlined inlet and outlet end;
    each end having an inner surface portion defining an annular valve seat;
    closure means, comprising a pair of streamlined valve members one of which is associated with each of said inlet and outlet end and disposed for operatively seating against the respective valve seat;
    releasable retaining means for releasably retaining the valve members away from its respective valve seat whereby the tubular member defines an open conduit prior to sample acquisition;
    a resilient connecting member biasing said valve members toward one another onto its respective seat, and operative to confine a sample within the tubular member upon release of said retaining means.

2. The apparatus of claim 1 wherein said resilient connecting member is hollow defining a passageway.

3. The apparatus of claim 2 wherein at least one of the valve members has a passageways that interconnects the passageway of the connecting member with a region outside of a confined sample within the tubular member.

4. The apparatus of claim 1 wherein each of said ends of said tubular member includes an enlarged tubular portion for surrounding a major portion of the respective valve member, and a converging transition portion the inner surface of which defines the valve seat.

5. The apparatus of claim 4 wherein the size and shape of an inner surface of the enlarged portion and the valve number are such that in an open position the cross-sectional area of a flow passage around the valve member is substantially constant.

6. The apparatus of claim 1 wherein each of the valve members include an annular seal for engagement with the respective valve seat.

* * * * *

UNITED STATES PATENT AND TRADEMARK OFFICE
CERTIFICATE OF CORRECTION

PATENT NO. : 4,846,004

DATED : July 11, 1989

INVENTOR(S) : D.L. Richards, H. Melling

It is certified that error appears in the above-identified patent and that said Letters Patent is hereby corrected as shown below:

In the drawing, Fig. 1, reference numeral "5" (left occurrence), designating the open position of valve number 5, should read -- 15 --; reference numeral "5'" (both occurrences) designating the closed position of valve member 5 should read -- 15' --; and, insert a reference numeral -- 5 -- with lead line leading to the left valve member which is similar and opposite to the valve member shown at the right and also identified by reference numeral "5".

Column 1, line 10 "is" should read -- in --.

Column 2, line 19 (after "closed position"), "15" should read -- 15' --.

In Claim 1, column 4, line 9, after "having a", insert -- hydrodynamically --; column 4, line 10, after "outlet end", insert -- for providing hydrodynamically streamlined flow through the sampling bottle --; column 4, line 13, after "a pair of" insert -- hydrodynamically --; column 4, line 16, after "valve seat," insert -- and providing hydrodynamically streamlined flow through the sampling bottle when the valve members are in an open position --; and column 4, line 21, after "connecting member", insert -- interconnecting said valve members for --.

UNITED STATES PATENT AND TRADEMARK OFFICE
CERTIFICATE OF CORRECTION

PATENT NO. : 4,846,004

DATED : July 11, 1989

INVENTOR(S) : D.L. Richards, H. Melling

It is certified that error appears in the above-identified patent and that said Letters Patent is hereby corrected as shown below:

In Claims 2 to 6 inclusive, column 4, lines 26, 28, 33, 38 and 43, respectively, delete "apparatus", each occurrence, and insert -- sampling bottle --.

Signed and Sealed this

Fifteenth Day of May, 1990

Attest:

HARRY F. MANBECK, JR.

*Attesting Officer*    *Commissioner of Patents and Trademarks*